(12) United States Patent
Martin et al.

(10) Patent No.: US 8,287,547 B2
(45) Date of Patent: Oct. 16, 2012

(54) ADJUSTABLE DRILL GUIDE

(75) Inventors: Troy D. Martin, Warsaw, IN (US); Rebecca Zimmerman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1121 days.

(21) Appl. No.: 12/144,014

(22) Filed: Jun. 23, 2008

(65) Prior Publication Data
US 2009/0318927 A1 Dec. 24, 2009

(51) Int. Cl.
A61B 17/58 (2006.01)
A61F 2/00 (2006.01)
B23B 45/14 (2006.01)
B23B 49/00 (2006.01)
B27G 15/00 (2006.01)

(52) U.S. Cl. .......... 606/96; 408/110; 408/202; 408/203; 408/241 G (58) Field of Classification Search ............ 606/53, 606/79, 81, 86 R, 87, 88, 96, 80, 89, 97, 98, 606/104; 623/20.16; 408/241 B, 241 G, 408/241 S
See application file for complete search history.

(56) References Cited

U.S. PATENT DOCUMENTS

| | | | |
|---|---|---|---|
| 2,562,397 A * | 7/1951 | Seybold | 84/363 |
| 4,033,043 A | 7/1977 | Cunningham | |
| 5,053,037 A | 10/1991 | Lackey | |
| 5,100,408 A | 3/1992 | Lackey | |
| 5,282,803 A | 2/1994 | Lackey | |
| 5,415,663 A | 5/1995 | Luckman et al. | |
| 5,417,693 A | 5/1995 | Sowden et al. | |
| 5,514,140 A | 5/1996 | Lackey | |
| 5,520,692 A | 5/1996 | Ferrante | |
| 5,690,636 A | 11/1997 | Wildgoose et al. | |
| 5,735,856 A | 4/1998 | McCue et al. | |
| 5,788,701 A | 8/1998 | McCue | |
| 5,885,293 A | 3/1999 | McDevitt | |
| 5,910,143 A | 6/1999 | Cripe et al. | |
| 5,951,564 A | 9/1999 | Schroder et al. | |
| 5,976,147 A | 11/1999 | LaSalle et al. | |
| 6,024,746 A | 2/2000 | Katz | |
| 6,059,788 A | 5/2000 | Katz | |
| 6,063,091 A | 5/2000 | Lombardo et al. | |
| 6,077,270 A | 6/2000 | Katz | |
| 6,162,226 A | 12/2000 | DeCarlo, Jr. et al. | |
| 6,228,091 B1 | 5/2001 | Lombardo et al. | |

(Continued)

FOREIGN PATENT DOCUMENTS
WO 9920192 4/1999

OTHER PUBLICATIONS

European Search Report for European Patent Application No. 09162882.6-2310 / 2138110, Apr. 22, 2010, 5 pgs.

*Primary Examiner* — Alvin Stewart
*Assistant Examiner* — Yashita Sharma
(74) *Attorney, Agent, or Firm* — Barnes & Thornburg LLP (57) ABSTRACT

A drill guide for use with an orthopaedic drilling device includes a base and a sleeve movably coupled to the base. The base is configured to be coupled to a surgically-prepared surface of a patient's bone and includes cylindrical body defining a passageway therethrough and a pin coupled to the body. The sleeve includes a slot and the pin of the base is received through the slot of the sleeve.

10 Claims, 7 Drawing Sheets

U.S. PATENT DOCUMENTS

| | | |
|---|---|---|
| 6,258,095 B1 | 7/2001 | Lombardo et al. |
| 6,602,258 B1 | 8/2003 | Katz |
| 6,620,168 B1 | 9/2003 | Lombardo et al. |
| 6,673,077 B1 | 1/2004 | Katz |
| 6,740,092 B2 | 5/2004 | Lombardo et al. |
| 7,261,499 B2 * | 8/2007 | Mathis et al. ............ 408/202 |
| 2005/0124998 A1 | 6/2005 | Coon et al. |
| 2006/0089641 A1 | 4/2006 | Collazo |

* cited by examiner

ADJUSTABLE DRILL GUIDE

TECHNICAL FIELD

The present disclosure relates generally to an instrument for guiding an orthopaedic drilling device such as a reamer into a patient's bone, and particularly to an instrument for guiding and limiting the travel of the reamer as the reamer drills a cavity into the patient's bone is being reamed.

BACKGROUND

Orthopaedic surgeons develop openings or cavities in long bones for a variety of reasons including fracture fixation and the implantation of stem based prostheses. The bone receiving the stem is typically prepared by drilling a hole in the bone and creating an opening sized and contoured to receive the stem of the implant therein. Typically, surgeons must ream or drill the cavity into the bone to a suitable predetermined depth. Accordingly, surgeons have employed a variety of methods for indicating a predetermined reaming depth of a long bone orthopaedic drilling device, such as a reamer.

One such method includes marking the desired depth on the reamer with a pen so that the surgeon will know that the proper depth has been reached when the marking reaches the leading edge of the bone being reamed. Another method includes the use of reamers having specific depth markings or grooves thereon to provide a visual indicator to the surgeon of the depth of the reamer as the cavity is being drilled. Other methods include the use of a collar and/or a movable sleeve on the reamer which operate to prevent the drilling device from reaming beyond the predetermined reaming depth. For example, the collar may be adjustable along the length of the drilling device in order to vary the predetermined reaming depth. Similarly, a plurality of sleeves may be provided in order to vary the predetermined reaming depth. See, for example, U.S. Pat. No. 6,162,226.

SUMMARY

According to one aspect of the present disclosure, an adjustable drill guide for use with an orthopaedic drilling device includes a base and a sleeve coupled to the base for movement relative to the base. The base is configured to be coupled to a surgically-prepared surface of a patient's bone and includes a cylindrical body defining a passageway therethrough and a pin coupled to the body. The sleeve includes a slot and the pin of the base is received through the slot of the sleeve.

In one illustrative embodiment, the adjustable drill guide may further include a spring in contact with the base and the sleeve to bias the sleeve upwardly relative to the base. The spring may be a coil spring. Further, the base may include an inner rim and the sleeve may include a spring hub such that a first end of the spring may contact the inner rim of the base and a second end of the spring may contact the spring hub of the sleeve.

In another illustrative embodiment, the sleeve may be positioned around the cylindrical body of the base.

In yet another illustrative embodiment, the sleeve may include a plurality of slots. Further illustratively, the plurality of slots may be open to each other. Each of the slots of the plurality of slots (i) may also be parallel to each other and (ii) may define a length different from each other slot of the plurality of slots.

In still another illustrative embodiment, the base may further include a flange having an aperture formed therein. The aperture of the flange may be configured to receive a bone nail therethrough in order to secure the base to the patient's bone.

In another illustrative embodiment, the sleeve may be movable upwardly and downwardly relative to the base along the longitudinal axis of the cylindrical body of the base. Further illustratively, the sleeve may be rotatable relative to the base about the longitudinal axis of the cylindrical body of the base.

According to another aspect of the present disclosure, an adjustable drill guide for use with an orthopaedic drilling device includes a base and a sleeve coupled to the base. The base is configured to be coupled to a surgically-prepared surface of a patient's bone and defines a passageway configured to receive the orthopaedic drilling device therethrough. The sleeve defines a passageway and the base is positioned within the passageway. Illustratively, the sleeve is both rotatable relative to the base about the longitudinal axis of the cylindrical body of the base and is movable upwardly and downwardly along the longitudinal axis relative to the base.

In one illustrative embodiment, the adjustable drill guide may also include (i) a slot formed in one of the sleeve and the base and (ii) a pin coupled to the other of the sleeve and the base. The pin may be received within the slot. For example, the slot may be formed in the base and the pin may be coupled to the sleeve. Alternatively, the slot may be formed in the sleeve and the pin may be coupled to the base. Further illustratively, the adjustable drill guide may include a plurality of slots formed in one of the sleeve and the base. Each such slot of the plurality of slots may define a longitudinal axis parallel to the longitudinal axis of the base.

In another illustrative embodiment, the adjustable drill guide may also include a spring positioned between the base and the sleeve. The spring may be configured to bias the sleeve upwardly relative to the base.

In yet another illustrative embodiment the sleeve may be is rotatable relative to the base between (i) a first position wherein the sleeve is movable upwardly and downwardly relative to the base a first distance and (ii) a second position wherein the sleeve is movable upwardly and downwardly relative to the base a second distance smaller than the first distance. Illustratively, the sleeve may be rotatable relative to the base to a third position wherein the sleeve is movable upwardly and downwardly relative to the base a third distance smaller than the second distance.

According to still another aspect of the present disclosure, a method of guiding an orthopaedic drilling device for drilling a cavity into a surgically-prepared surface of a patient's bone includes securing an adjustable drill guide to the patient's bone, adjusting the drill guide to one of a first position corresponding to a first depth of a cavity to be drilled into the patient's bone and a second position corresponding to a second depth of the cavity to be drilled into the patient's bone, and inserting the orthopaedic drilling device into the adjustable drill guide. The method further includes moving the orthopaedic drilling device and a sleeve of the adjustable drill guide relative to a base of the adjustable drill guide as the orthopaedic drilling device drills into the patient's bone, and limiting the movement of the sleeve relative to the base to prevent further drilling of the cavity by the orthopaedic drilling device.

BRIEF DESCRIPTION OF THE DRAWINGS

The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Figure 4:
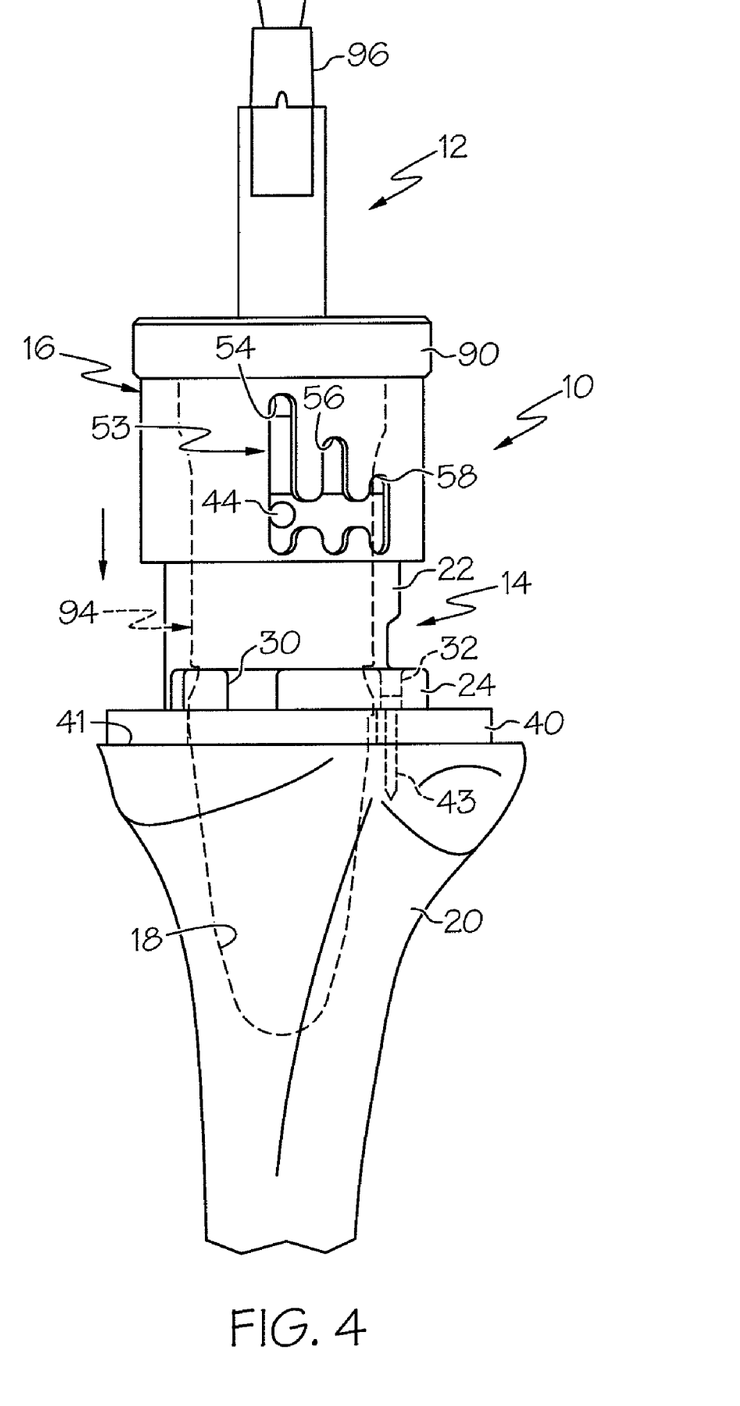
FIG. 4 is a side view similar to FIG. 3 showing a collar of the reamer in contact with and pushing down on a movable sleeve of the guide as the reamer drills a cavity into the patient's bone.

An adjustable drill guide 10 for guiding an orthopaedic drilling device such as a reamer 12 includes a base 14 and a sleeve 16 coupled to the base 14 for up and down axial movement relative to the base 14. As is discussed in greater detail below, the sleeve 16 is also rotatably movable relative to the base 14. Illustratively, the drill guide 10 operates to guide the reamer 12 as the reamer 12 drills a cavity 18 within a patient's tibia 20, as shown in FIG. 4, and also operates to limit the distance the reamer 12 is able to travel into the patient's tibia 20 in order to control and limit the depth of the resulting cavity 18.

Figure 1:
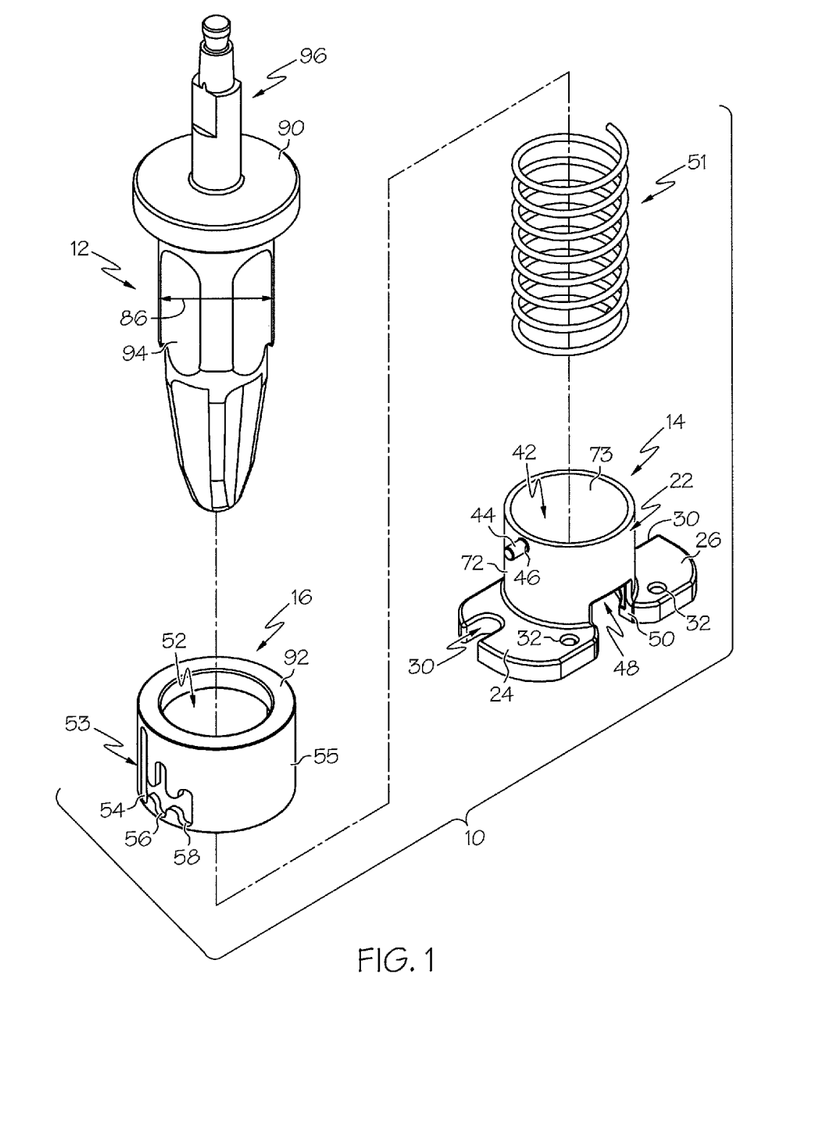
FIG. 1 is an exploded perspective view of one embodiment of an intramedullary (IM), long bone reamer and an adjustable guide.
Figure 2:
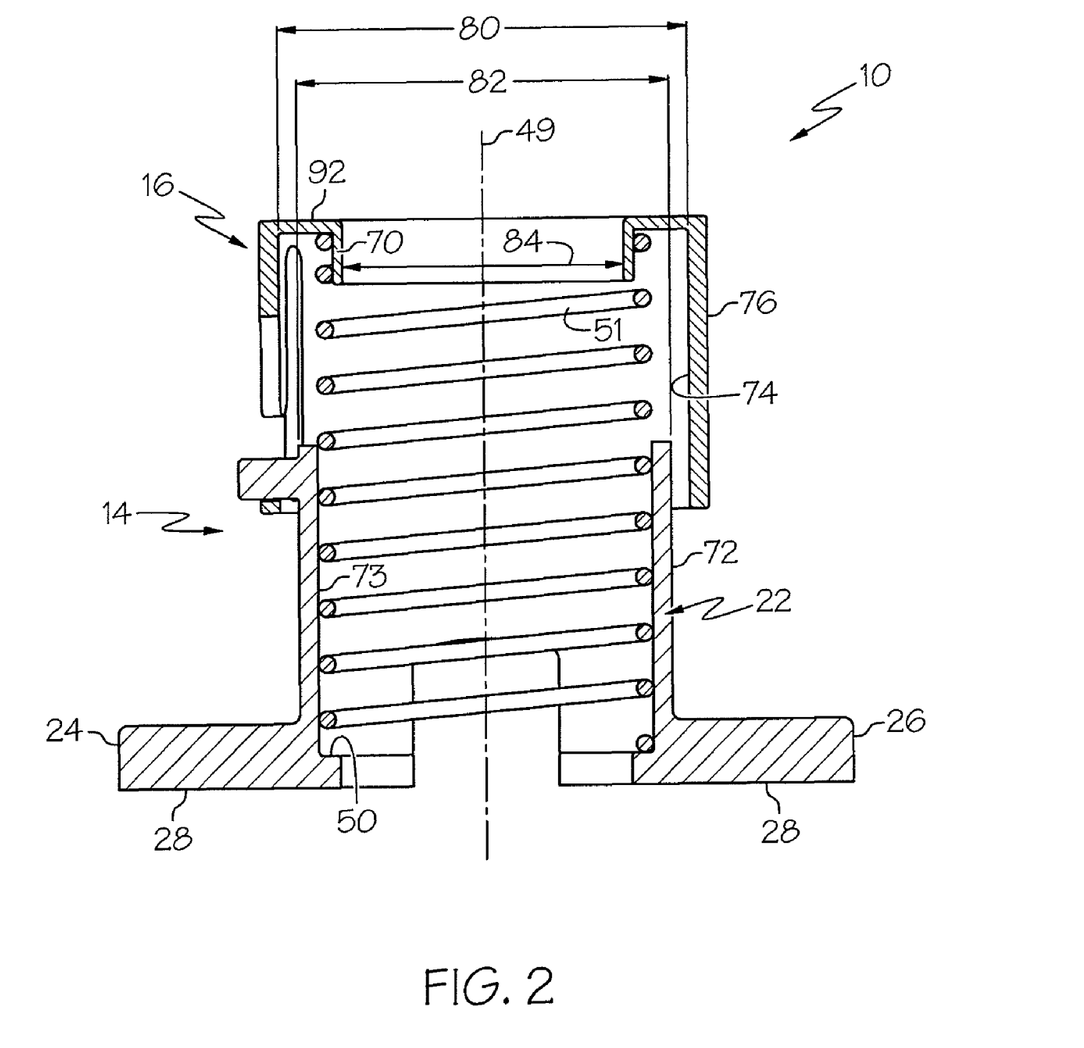
FIG. 2 is a sectional view of the assembled adjustable guide of FIG. 1.
Figure 3:
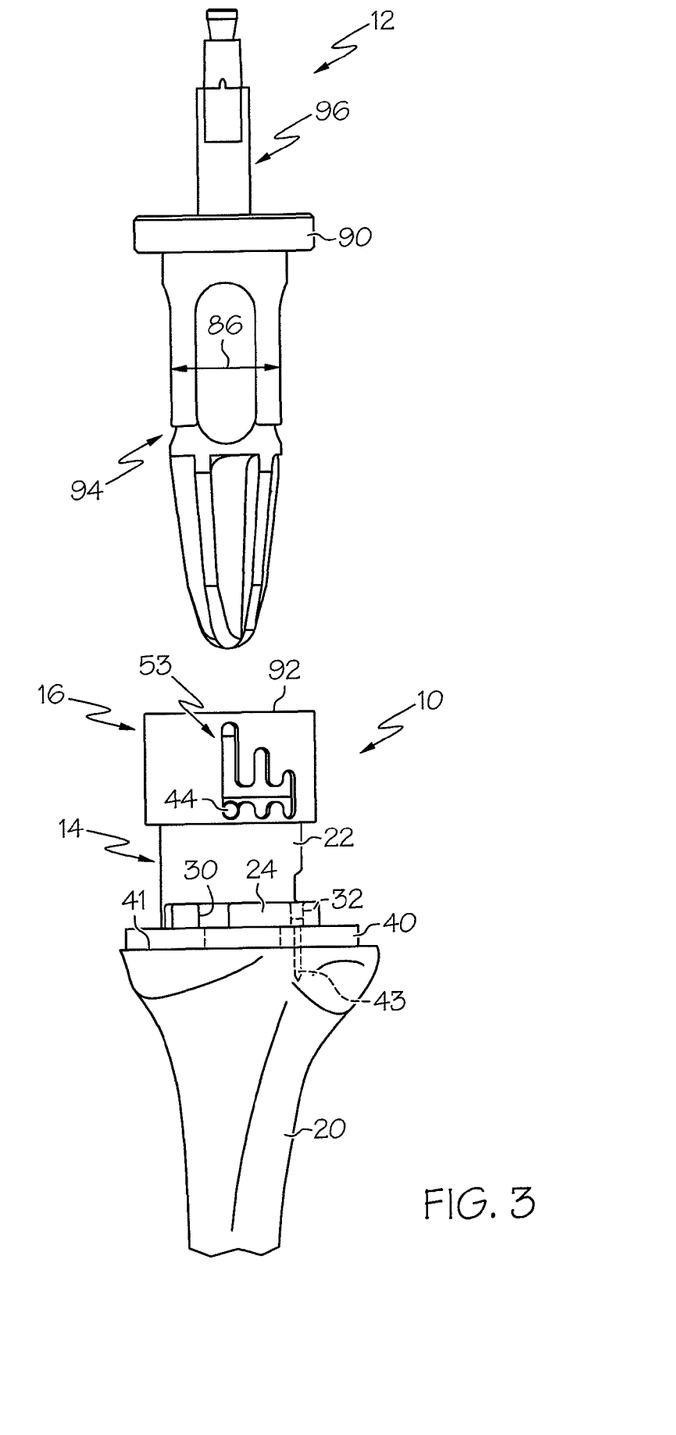
FIG. 3 is a side view showing the adjustable guide of FIGS. 1 and 2 positioned on a tibial trial tray on the generally flat surgically-prepared surface of a resected tibia and showing the reamer about to be inserted into the guide.
Figure 5:
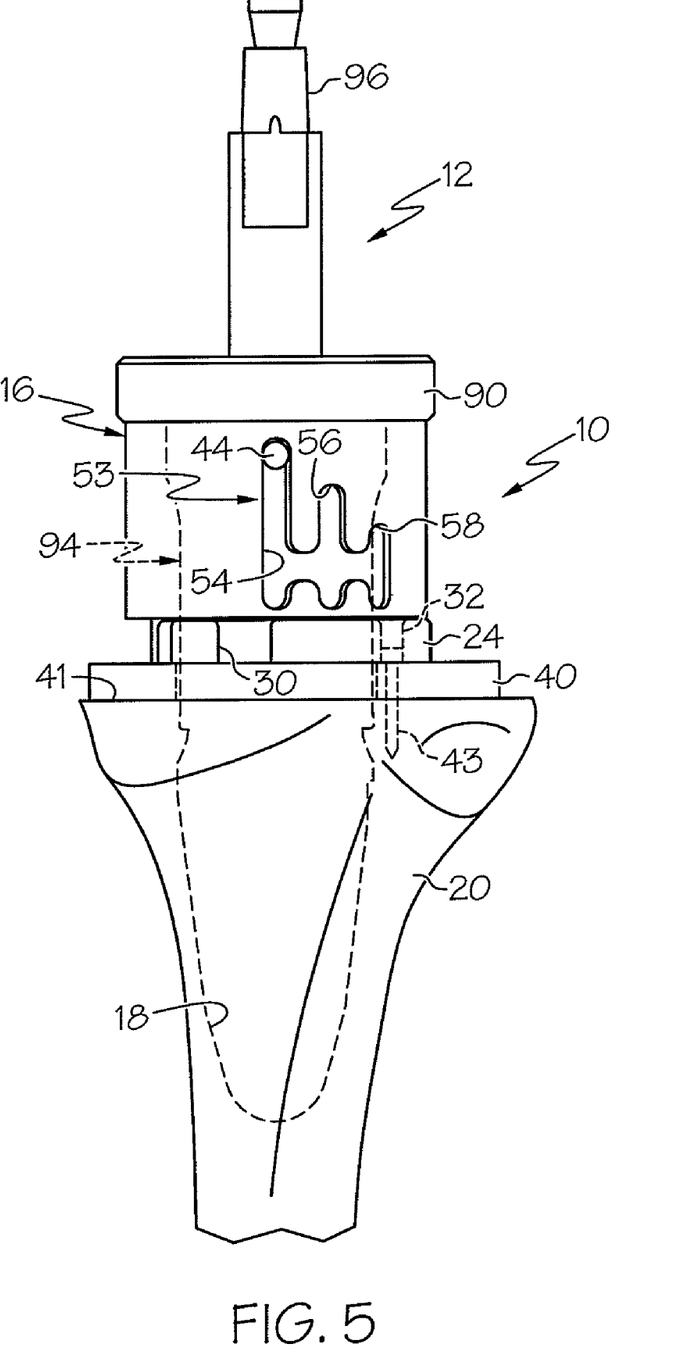
FIG. 5 is a side view similar to FIG. 4 showing the guide in a travel-limit position to prevent the reamer from drilling any further within the patient's bone.

As shown in FIGS. 1 and 2, the drill guide 10 includes the base 14 and the sleeve 16. The base 14 includes a cylindrical body 22 and first and second flanges 24, 26 coupled to a bottom end of the base 14. Each of the first and second flanges 24, 26 defines a generally flat bottom surface 28. Further illustratively, each flange 24, 26 includes a cut-out portion 30 and an aperture 32. As is discussed in greater detail below, the flat bottom surface 28 of the flanges 24, 26 is configured to rest on at least a portion of a tibial trial tray 40 positioned on a surgically-prepared surface 41 of the patient's resected tibia 20. Of course, the flanges 24, 26 may be configured to rest directly on the surface 41 of the patient's tibia 20 as well. The cut-out portion 30 provides clearance for a portion of the tibial trial tray 40 upon which the base 14 is positioned. Each aperture 32 receives a bone nail 43 therethrough in order to secure the base 14 to the tray 40 and the resected tibia 20, as shown in FIGS. 3-5. As such, the base 14 itself is configured to be secured to the surgically-prepared surface 41 of the patient's tibia 20.

The cylindrical body 22 of the base 14 includes an outer surface 72 and an inner surface 73 defining a passageway 42 therethrough. A pin 44 of the base 14 is coupled to the outer surface 72 of the body 22, as shown in FIG. 1. Illustratively, the pin 44 is received through an aperture 46 formed in the body 22 of the base 14 and is secured thereto by a press-fit or threaded connection. However, it is within the scope of this disclosure to secure the pin 44 to the body 22 of the base 14 using any suitable fastener. During assembly, the pin 44 may be inserted into the aperture 46 of the base 14 after the sleeve 16 is positioned around the body 22 of the base 14. Alternatively, the pin 44 may be formed as a unitary structure with the body 22 of the base 14.

The body 22 of the base 14 further includes a notch 48 positioned between the flanges 24, 26. Similar to the cut-out portions 30 of the flanges 24, 26, the notch 48 is configured to provide clearance for one or more portions of the tibial trial tray 40 upon which the base 14 is positioned. Illustratively, the pin 44 and cut-out portion 30 of the flange 24 of the base 14 are generally aligned with each other such that the pin 44 is spaced-apart from and generally positioned above the cut-out portion 30 of the flange 24. Of course, it is within the scope of this disclosure to provide a base having a pin in another suitable location. Finally, as shown in FIG. 1, the base 22 further includes an inner rim 50 positioned at the bottom or distal end of the body 22 that is adjacent the flanges 24, 26. As is discussed in greater detail below, the inner rim 50 supports a spring 51 of the guide 10 thereon in order to bias the sleeve 16 upwardly relative to the base 14.

The sleeve 16 is coupled to the base 14 and movable relative to the base 14 upwardly and downwardly along a longitudinal axis 49 of the body 22 of the base 14 and the guide 10 (shown in FIG. 7) as well as rotationally in both clockwise and counterclockwise directions about the longitudinal axis 49. Illustratively, the sleeve 16 is cylindrical in shape and includes a sidewall 55 defining a passageway 52 therethrough. The sleeve 16 further includes a cut-out portion 53 formed in the sidewall 55. Illustratively, as shown best in FIGS. 5 and 6, the cut-out portion 53 includes a first slot 54, a second slot 56, and a third slot 58. The first, second, and third slots 54, 56, 58 are each parallel to each other and parallel to the longitudinal axis 49 of the guide 10. Illustratively, the first and second slots 54, 56 are open to each other via a first passageway 60. Similarly, the second and third slots 56, 58 are open to each other via a second passageway 62. Accordingly, the first, second, and third slots 54, 56, 58 are all open one another.

Figure 6:
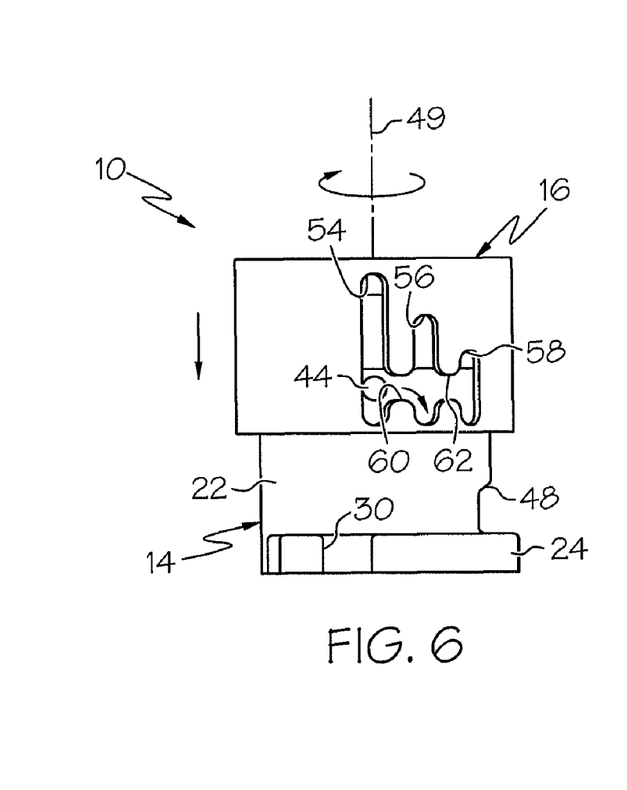
FIGS. 6 and 7 are side views of the adjustable guide of FIGS. 1-5 showing a sleeve of the guide being rotated to a second position relative to a base of the guide to adjust the amount of relative movement between the sleeve and the base.
Figure 7:
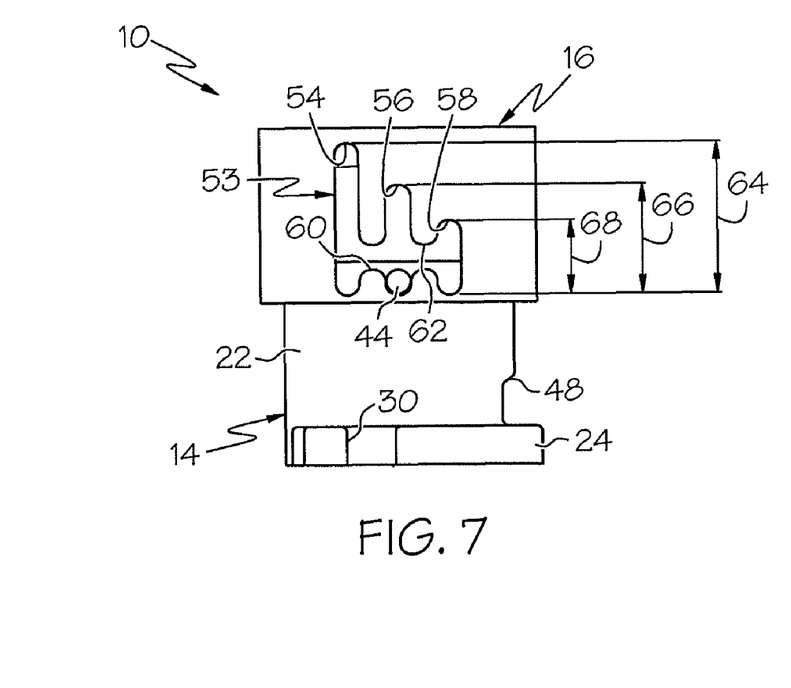

Illustratively, the respective length of each slot 54, 56, 58 corresponds to the depth of the cavity 18 to be formed by the reamer 12. As shown in FIG. 7, a length 64 of the first slot 54 is greater than a length 66 of the second slot 56 and the length of the second slot 56 is greater than a length 68 of the third slot 58. Illustratively, the distal ends of the first, second, and third slots 54, 56, 58 are generally aligned with each other such that the distal ends of each slot 54, 56, 58 are spaced an equal distance away from the distal end of the sleeve 16. However, the proximal end of the third slot 58 is spaced farther apart from the proximal end of the sleeve 16 than the proximal end of the second slot 56 and the proximal end of the second slot 56 is spaced farther apart from the proximal end of the sleeve 16 than the proximal end of the first slot 54. While the particular cut-out portion 53 of the sleeve 16 is described above and shown in FIGS. 1 and 3-7 herein, it is within the scope of this disclosure to include a sleeve having any suitable cut-out portion formed therein. In other words, it is within the scope of this disclosure to include a sleeve having any number of slots in any number of sizes. Furthermore, it is within the scope of this disclosure for such slot or slots to be positioned in any location on the sleeve.

As noted above, the guide 10 of the present disclosure further includes the spring 51. Illustratively, the spring 51 is a coil spring having a first end in contact with the base 14 and a second end in contact with the sleeve 16. As shown in FIG. 2, the first or lower end of the spring 51 rests upon the inner rim or ledge 50 of the base 14 while the second or upper end of the spring 51 is positioned around a spring hub 70 at the upper or proximal end of the sleeve 16. Accordingly, the spring 51 operates to bias the sleeve 16 upwardly relative to the base 14. While the spring 51 is shown to be positioned inside the passageway 42 of the base 14 and the passageway 52 of the sleeve, it is within the scope of this disclosure to position the spring 51 around the outer surface 72 of the cylindrical body 22 of the base 14. For example, a distal end of the spring 51 may be coupled to or rest on the flanges 24, 26 of the base 14 or may be coupled to the distal end of the body 22 of the base 14 while a proximal end of the spring may be coupled to or rest against the distal end of the sleeve 16 in order to bias the sleeve 16 upwardly relative to the base 14. Further, while the particular coil spring 51 is provided, it is within the scope of this disclosure to couple any suitable spring to the base 14 and sleeve 16 in any suitable location in order to bias the sleeve 16 upwardly relative to the base 14.

In use, the sleeve 16 is positioned around the body 22 of the base 14 such that the outer surface 72 of the body 22 of the base 14 is adjacent, but not necessarily in contact with, an inner surface 74 of the sidewall 55 of the sleeve 16. Illustratively, an inner diameter 80 of the sidewall 55 of the sleeve 16 is generally equivalent to an outer diameter 82 of the body 22 of the base 14. As shown in FIG. 2, the outer diameter 82 of the body 22 of the base 14 may be slightly smaller than the inner diameter 80 of the sleeve 16. However, it is within the scope of this disclosure to minimize the difference between the diameters 80, 82 in order to minimize any wobble of the sleeve 16 relative to the base 14 as the sleeve 16 moves upwardly and downwardly relative to the base 14. Preventing any such wobble of the sleeve 16 may aide in guiding the reamer 12 along the axis 49 while drilling the cavity 18. Further illustratively, an inner diameter 84 of the spring hub 70 of the sleeve 16 is generally equivalent to the outer diameter 86 of a drill head 94 of the reamer 12 in order to further guide the reamer 12 along the axis 49 while drilling the cavity 18.

The pin 44 of the base 14 is received within the cut-out portion 53 of the sleeve 16 such that the pin 44 is positioned within one of the three slots 54, 56, 58. Illustratively, as shown in FIGS. 3-5, the pin 44 is positioned within the first slot 54. Further illustratively, because the sleeve 16 is biased upwardly by the spring 51, the pin 44 is in contact with a bottom surface of the slot 54, as shown in FIG. 3.

The respective length 64, 66, 68 of each slot 54, 56, 58 corresponds to the depth of the cavity to be formed by the reamer 12. In other words, the longer the slot 54, 56, or 58 within which the pin 44 is received, the deeper the cavity that will be formed by the reamer 12. As such, the guide 10 operates to limit the depth of the cavity to a distance equal to or directly proportional to the length of the slot 54, 56, 58 within which the pin 44 is located. For example, when the pin 44 of the base is positioned within the first slot 54, the sleeve 16 is in a first position and is able to move upwardly and downwardly relative to the base 14 a first distance equal to the length 64 of the slot 54. Similarly, when the pin 44 of the base 14 is positioned within the second slot 56 of the sleeve 16, the sleeve 16 is in a second position relative to the base 14 and is movable upwardly and downwardly relative to the base 14 a second distance equal to the length 66 of the second slot 56. When the pin 44 of the base 14 is positioned within the third slot 58, the sleeve 16 is in a third position relative to the base 14 and is movable upwardly and downwardly relative to the base 14 a third distance equal to the length 68 of the third slot 58. Accordingly, prior to the reaming procedure, the physician or other technician positions the pin 44 within the slot 54, 56, or 58 corresponding to the desired depth of the cavity 18 to be formed by the reamer 12.

Once the pin 44 is positioned within the desired slot 54, 56, 58, the guide 10 is positioned on the tibial trial tray 40 on the surgically-prepared surface 41 of a resected long bone such as the tibia 20, as shown in FIGS. 3-5. Illustratively, while the present disclosure describes the use of the guide 10 and reamer 12 to prepare a cavity in the resected tibia 20, it is within the scope of this disclosure to use the guide 10 and reamer 12 with any bone into which a cavity is to be formed. Once the guide 10 is properly positioned on the tray 40 on the resected tibia 20, the guide 10 is secured in place by one or more fasteners such as screws or illustrative bone nails 43 received through the apertures 32 formed in the flanges 24, 26 of the base 14.

Once the guide 10 has been secured to the tray 40 and the tibia 20, the reamer 12 is inserted into the passageway 52 of the sleeve 16 until the bottom surface of a collar 90 of the reamer 12 abuts a top surface 92 of the sleeve 16, as shown in FIG. 3. Illustratively, the reamer 12 shown in FIGS. 1 and 2 includes the drill head 94, the collar 90 coupled to the drill head 94, and a shank 96 configured to be received within a chuck of a motorized portion of the drilling device (not shown). Further illustratively, the collar 90 is rigidly fixed on the drill head 94 and shank 96 and is not adjustable between multiple locations along the shank 96 of the reamer 12. However, it is within the scope of this disclosure to include a reamer 12 having an adjustable collar mounted thereon. Further illustratively, while the particular reamer 12 is shown in FIGS. 1 and 2, it is within the scope of this disclosure to include any suitable orthopaedic drilling device including a drill bit able to received within the respective passageways 42, 52 of the base 14 and the sleeve 16 as well as a flange or collar able to contact the top surface 92 of the sleeve 16 as the drilling device is moved downwardly into the patient's bone.

Looking new to FIGS. 4 and 5, as the surgeon or other technician continues to press the reamer 12 downwardly, the sleeve 16 is also moved downwardly against the bias of the spring 51. The downward motion of the sleeve 16 is constrained by the pin 44 and the slot 54 of the sleeve 16 within which the pin 44 is received. Accordingly, the slot 54 and pin 44 cooperate to maintain the movement of the sleeve 16, and therefore, the movement of the reamer 12, in a vertical, non-angled direction collinear with axis 49 of the guide 10. Furthermore, the length 64 of the slot 58 operates to limit the depth of the cavity 18 being formed by the reamer 12. As such, as the reamer 12 drills deeper into the tibia 20, the reamer 12 urges the sleeve 16 downwardly in a distal direction toward the tibia 20 until the pin 44 contacts the upper, or proximal, end of the slot 54, as shown in FIG. 5. Once the pin 44 contacts the upper end of the slot 54, the reamer 12 is prevented from drilling any deeper into the tibia 20. Accordingly, the guide 10 operates as a travel-limit stop for limiting the downward movement of the reamer 12 into the patient's bone 20. Once the cavity 18 has been drilled, the surgeon may remove the reamer 12 from the guide 10 and may remove the guide 10 from the tray 40 on the surgically-prepared surface 41 of the resected tibia 20.

As discussed above, the guide 10 is adjustable to allow the surgeon to select the depth of the cavity 18 to be drilled. Illustratively, the guide 10 is adjustable between first, second, and third positions. As shown in FIGS. 3-5, the guide 10 is in the first position wherein the pin 44 of the base 14 is received within the first slot 54 of the cut-out portion 53 of the sleeve 16. As discussed above, the sleeve 16 is moveable up and down relative to the base 14 while maintaining the pin 44 within the first slot 54. As shown in FIGS. 6 and 7, guide 10 may be adjusted to the second position wherein the pin 44 of the base 14 is received within the second slot 56 of the sleeve 16. Illustratively, in order to adjust the guide 10 from the first position (shown in FIG. 6) to the second position (shown in FIG. 7), the user depresses the sleeve 16 against the bias of the spring 51 until the pin 44 of the base 14 is aligned with the first passageway 60 of the cut-out portion 53 of the sleeve 16. Once aligned, the user may rotate the sleeve 16 in a clockwise direction to position the pin 44 of the base 14 within the second slot 56 of the sleeve 16.

In order to adjust the guide 10 to a third position, the user may again depress the sleeve 16 against the bias of the spring 51 until the pin of the base 14 (now located within second slot 56) is aligned with the first and second passageways 60, 62 of the cut-out portion 53. At this point, the user may rotate the sleeve 16 clockwise to position the pin 44 within the third slot 58. Alternatively, the user may rotate the sleeve 16 counterclockwise to again position the pin 44 within the first slot 54 to orient the guide 10 in the first position. Accordingly, the sleeve 16 is rotatable both clockwise and counterclockwise in order to position the pin 44 of the base 14 within one of the slots 54, 56, 58 provided.

Figure 8:
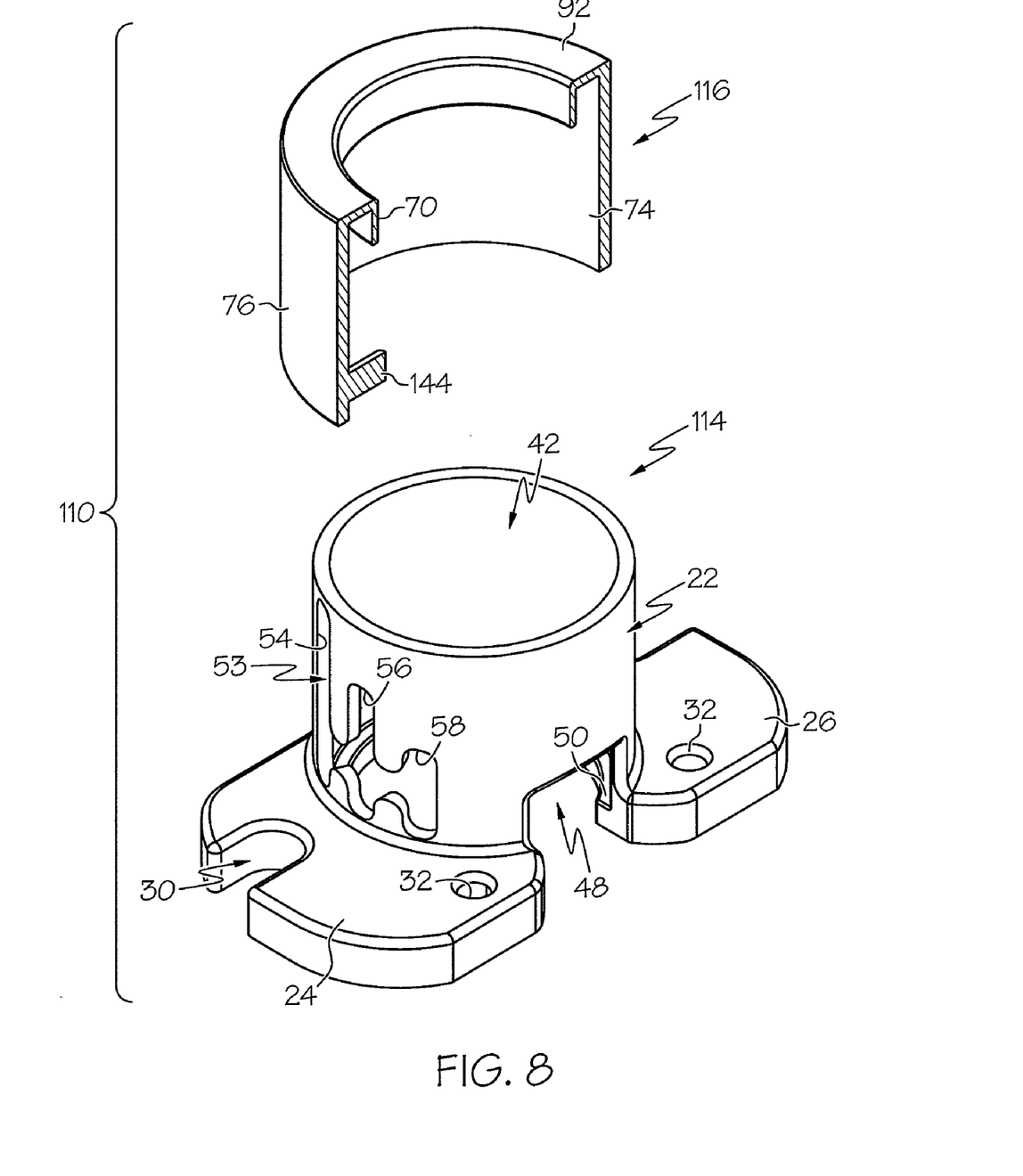
FIG. 8 is a perspective view of another adjustable guide of the present disclosure.

Looking now to FIG. 8, an alternative guide 110 is provided. The guide 110 is similar to the guide 10 shown in FIGS. 1-7 and discussed above. Accordingly, the same or similar reference numbers are used to designate the same or similar features. The guide 110 includes a base 114 similar to the base 14, a sleeve 116 similar to the sleeve 16, and the spring 51 (not shown in FIG. 8). However, the cylindrical wall 22 of the base 114 includes the cut-out portion 53 formed therein and the sleeve 116 includes a pin 144 extending inwardly from the inner surface 74 of the sleeve 116. Illustratively, the pin 144 is shown as a unitary structure with the sleeve 116. However, is within the scope of this disclosure for the pin 144 to be a separate structure coupled to the cylindrical wall of the sleeve 116 after the sleeve 116 is positioned onto the base 114, for example.

As with the guide 10 described above, the pin 144 of the guide 110 is received within the cut-out portion 53. In contrast to the guide 10, however, the spring (not shown for clarity) of the guide 110 may be positioned around an outside surface 76 of the sleeve 116 such that an upper end of the spring is coupled to the sleeve 116 and a lower end of the spring is coupled to the base 114 in order to bias the sleeve 116 upwardly relative to the base 114. As discussed above in regards to the guide 10, the spring of the guide 110 may be positioned in any suitable location to bias the sleeve 116 upwardly relative to the base 114.

Illustratively, the operation of the guide 110 is the same as or similar to that of the guide 10. For example, the sleeve 116 moves upwardly and downwardly relative to the base 114. This up and down motion of the sleeve 116 is both guided by and limited by the cut-out portion 53 and the pin 144 within the selected slot 54, 56, 58 of the cut-out portion 53. Further, the user is able to change the position of the sleeve 116 of the guide 110 between the first, second, and third positions by rotating the sleeve 116 relative to the base 114 in either a clockwise or counterclockwise direction when the pin 144 is located within one of the channels 60, 62 of the cut-out portion 53 of the base 114. Illustratively, the sleeve 116 may include an indicator or marking on the outer surface 76 of the sleeve 116 in order to denote the location of the pin 144 to the user.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. An adjustable drill guide for use with an orthopaedic drilling device comprising:
   a base configured to be coupled to a surgically-prepared surface of a patient's bone, the base including (i) a cylindrical body defining a first passageway therethrough and (ii) a pin extending away from the body;
   a sleeve coupled to the base for movement relative to the base, the sleeve including (i) a body defining a second passageway therethrough and (ii) an inner wall forming a slot in the body;
   a spring in contact with the base and the sleeve to bias the sleeve upwardly relative to the base,
   wherein (i) the pin of the base is received in the slot of the sleeve and is moved along the slot when the sleeve is moved relative to the base, and (ii) the pin is biased into engagement with a bottom surface of the inner wall to prevent movement of the sleeve beyond a predetermined position.

2. The adjustable drill guide of claim 1, wherein the spring is a coil spring.

3. The adjustable drill guide of claim 1, wherein the base includes an inner rim and the sleeve includes a spring hub such that a first end of the spring is in contact with the inner rim of the base and a second end of the spring is in contact with the spring hub of the sleeve.

4. The adjustable drill guide of claim 1, wherein the sleeve is positioned around the cylindrical body of the base.

5. The adjustable drill guide of claim 1, wherein the sleeve includes a plurality of slots.

6. The adjustable drill guide of claim 5, wherein the plurality of slots are open to each other.

7. The adjustable drill guide of claim 5, wherein each of the slots of the plurality of slots (i) are parallel to each other and (ii) define a length different from each other slot of the plurality of slots.

8. The adjustable drill guide of claim 1, wherein the base further includes a flange having an aperture formed therein, wherein the aperture is configured to receive a bone nail therethrough in order to secure the base to the patient's bone.

9. The adjustable drill guide of claim 1, wherein the sleeve is movable upwardly and downwardly relative to the base along the longitudinal axis of the cylindrical body of the base.

10. The adjustable drill guide of claim 1, wherein the sleeve is rotatable relative to the base about the longitudinal axis of the cylindrical body of the base and wherein the sleeve is movable upwardly and downwardly along the longitudinal axis relative to the base.

* * * * *